(12) United States Patent
Liu et al.

(10) Patent No.: US 10,188,765 B2
(45) Date of Patent: Jan. 29, 2019

(54) SUPER DRY FOG GENERATOR

(71) Applicant: HUBEI HOPE PHARMACEUTICAL CO., LTD., Hubei (CN)

(72) Inventors: Wanzhong Liu, Hubei (CN); Mingfang Bie, Hubei (CN); Chao Zhang, Hubei (CN)

(73) Assignee: HUBEI HOPE PHARMACEUTICAL CO., LTD., Hubei (CN)

( * ) Notice: Subject to any disclaimer, the term of this patent is extended or adjusted under 35 U.S.C. 154(b) by 124 days.

(21) Appl. No.: 15/315,693

(22) PCT Filed: Jun. 28, 2016

(86) PCT No.: PCT/CN2016/087405
§ 371 (c)(1),
(2) Date: Dec. 1, 2016

(87) PCT Pub. No.: WO2017/128610
PCT Pub. Date: Aug. 3, 2017

(65) Prior Publication Data
US 2017/0266331 A1    Sep. 21, 2017

(30) Foreign Application Priority Data
Jan. 28, 2016   (CN) .......................... 2016 1 0058240

(51) Int. Cl.
*A61L 9/00* (2006.01)
*B01D 47/00* (2006.01)
(Continued)

(52) U.S. Cl.
CPC .................. *A61L 2/22* (2013.01); *A61L 2/26* (2013.01); *A61L 9/14* (2013.01); *A61L 2202/15* (2013.01); *A61L 2202/16* (2013.01)

(58) Field of Classification Search
CPC ........... A61L 2/208; A61L 2/06; A01N 25/06; A01N 59/00
(Continued)

(56) References Cited

U.S. PATENT DOCUMENTS

2008/0292498 A1    11/2008   Resch et al.

FOREIGN PATENT DOCUMENTS

| CN | 101237894 | * | 8/2008 | ............... A61L 9/00 |
| CN | 101237894 A | | 8/2008 | |

(Continued)

OTHER PUBLICATIONS

European Patent Office English Translation of the claims, Drawings and Description Sections of CN 101237894.*
(Continued)

*Primary Examiner* — Monzer R Chorbaji
(74) *Attorney, Agent, or Firm* — Nath, Goldberg & Meyer; Tanya E. Harkins; Joshua B. Goldberg

(57) ABSTRACT

The present invention disclosed a super dry fog generator comprising a liquid-storage device, an atomization device, an air-blower and a dry separation device with an opening on the top; wherein said dry separation device is above said liquid-storage device and connected with said liquid-storage device; said atomization device is located at the exterior of said liquid-storage device; the two ends of said atomization device are connected with said air-blower and the interior of said dry separation device, respectively; said atomization device is connected with said liquid-storage device, and the liquid entering into the interior of said atomization device is blown into the interior of said dry separation device by said air-blower. The disinfection liquid entering into the atomization device from the liquid-storage device is atomized into small atomized liquid particles by the atomization device, and then the small atomized liquid particles are driven into (Continued)

the dry separation device by said air-blower. After being dried, the small atomized liquid particles are discharged to a space intended to be disinfected, then the disinfection is carried out. The small atomized liquid particles produced by the super dry fog generator of the present invention, whose size is small and much closer to the bacterial size, can be suspended in air for a long time so as to contact fully with the bacteria in air to achieve the purpose of sterilization, and they are convenient and safe with the less corrosion to the objects in the disinfection space.

9 Claims, 1 Drawing Sheet

(51) Int. Cl.
*B03C 3/00* (2006.01)
*A61L 2/22* (2006.01)
*A61L 9/14* (2006.01)
*A61L 2/26* (2006.01)

(58) Field of Classification Search
USPC .... 422/120, 123–125, 306; 96/15, 108, 243; 261/75
See application file for complete search history.

(56) References Cited

FOREIGN PATENT DOCUMENTS

| | | |
|---|---|---|
| CN | 104984378 A | 10/2015 |
| GB | 2483552 A | 3/2012 |
| WO | 2017128610 A1 | 8/2017 |

OTHER PUBLICATIONS

Supplementary European search report dated Jul. 21, 2017 for corresponding application No. EP 16 82 0143.
Written opinion of the International Search Authority dated Nov. 9, 2016 for corresponding application No. PCT/CN2016/087405 with English translation attached.
International search report dated Nov. 9, 2016 for corresponding application No. PCT/CN2016/087405 with English translation attached.

* cited by examiner

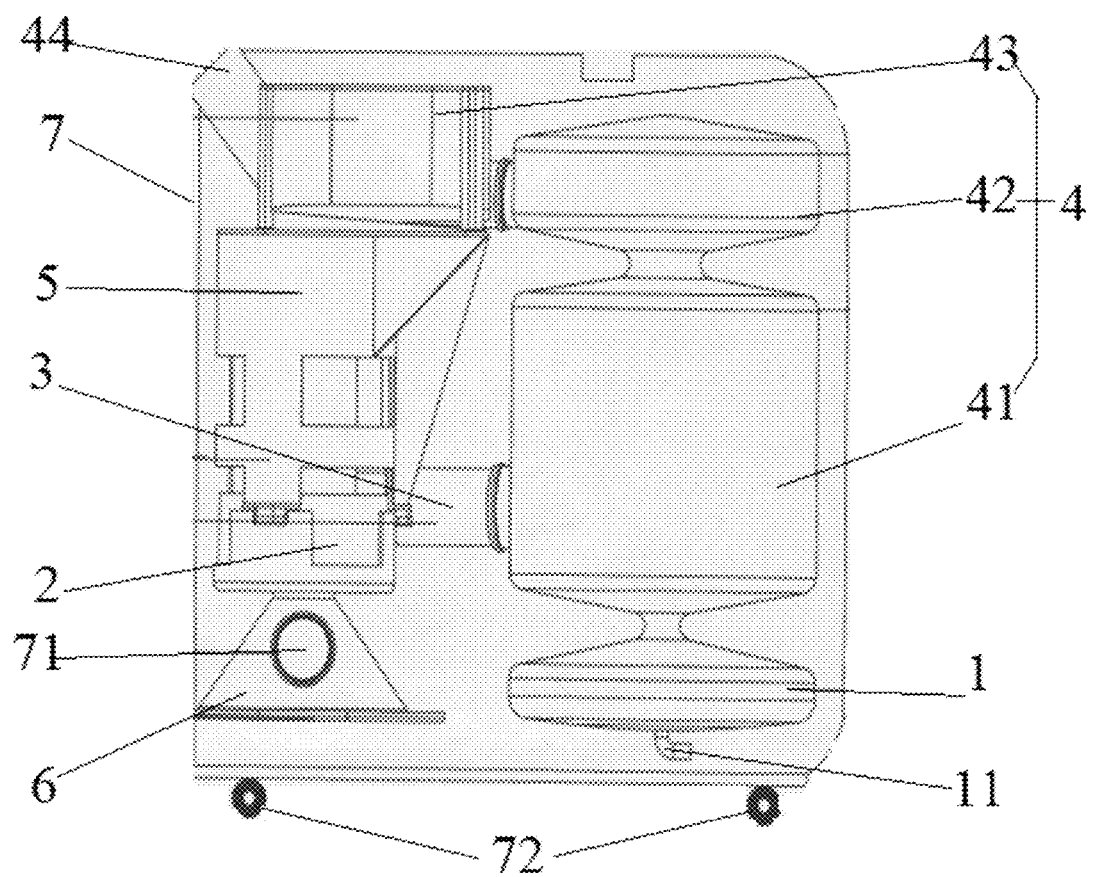

SUPER DRY FOG GENERATOR

This is a National Phase Application filed under 35 U.S.C. 371 as a national stage of PCT/CN2016/087405, filed Jun. 28, 2016, an application claiming the benefit of Chinese Application No. 201610058240.6, filed Jan. 28, 2016, the content of each of which is hereby incorporated by reference in its entirety.

TECHNICAL FIELD

The present invention relates to the field of health care disinfection, and specifically relates to a super dry fog generator.

TECHNICAL BACKGROUND

Microorganisms exist widely in nature, and in suitable environment they grow rapidly, causing the contamination. Therefore, in some specialty some circumstances the disinfection and sterilization become necessary.

The work of the disinfection and sterilization is necessary in the pharmaceutical industry. Currently, the disinfection and sterilization for Good Manufacturing Practice (GMP) workshop are carried out by means of formaldehyde fumigation and ozone or ultraviolet light in most of Chinese enterprises. Although formaldehyde fumigation is a high level sterilization method, the toxicity of formaldehyde is high. The long-term contact with formaldehyde in low concentration can cause headache, dizziness, fatigue, feeling obstacle, low-immunity, drowsiness, deterioration of the memory, neurasthenia, or mental depression. Chronic poisoning is greatly harmful for the respiratory system. The contact with formaldehyde in long term can lead to respiratory dysfunction and hepatic toxic lesion manifested by liver cell injury and abnormal radiation energy of liver etc, so formaldehyde fumigation has been forbidden to be used in GMP workshop in developed country. Ozone or ultraviolet light is safety, but the microbes can be only decreased partly. As a low level sterilization method, it is difficult to achieve the purpose for killing the microbes.

In the process of implementation of the present invention, the present inventors found that there are at least one of the following problems existed in the prior technology:

poor effect on disinfection, high toxicity, or a long-time disinfection.

SUMMARY OF THE INVENTION

In order to solve the problems of poor effect on disinfection, long-time disinfection, and high toxicity present in the prior technology, the present invention provides a super dry fog generator. The technical solution is as follows:

A super dry fog generator comprising a liquid-storage device, an atomization device, an air-blower and a dry separation device with an opening on the top; wherein said dry separation device is above said liquid-storage device and connected with said liquid-storage device; said atomization device is located at the exterior of said liquid-storage device; the two ends of said atomization device are connected with said air-blower and the interior of said dry separation device, respectively; said atomization device is connected with said liquid-storage device, and the liquid entering into the interior of said atomization device is blown into the interior of said dry separation device by said air-blower.

Preferably, said dry separation device comprises at least two connected cavity structures; the bottom of said dry separation device is joined to the top of said liquid-storage device and connected with the interior of said liquid-storage device.

Preferably, said dry separation device comprises a first cavity structure, a second cavity structure and a third cavity structure which are connected in sequence from bottom to top; said first cavity structure, said second cavity structure and said liquid-storage device are in an integrated structure, and said second cavity structure and said third cavity structure are movably joined; said opening is on the top of said third cavity structure.

Preferably, said atomization device is an atomizing nozzle, and said air-blower is a high-speed hot air motor.

Preferably, the inlet of said atomizing nozzle is connected with the air outlet of said high-speed hot air motor, and the outlet of said atomizing nozzle is connected with the interior of said first cavity structure.

Preferably, there is a through-hole at the bottom of said liquid-storage device, and said through-hole is connected with the interior of said atomizing nozzle via a tube; the liquid from the interior of said liquid-storage device enters into the interior of said atomizing nozzle after passing through said through-hole and said tube.

Further, said super dry fog generator comprises a shell; said liquid-storage device, said atomization device, said air-blower and said dry separation device are all in the interior of said shell; there is a perforation on said shell, and the air inlet of said high-speed hot air motor is connected with the environment through said perforation.

Further, said super dry fog generator comprises a first bracket and a second bracket; said first bracket is between the bottom plate of the interior of said shell and said air-blower so as to support said air-blower; said second bracket is between said air-blower and said third cavity structure so as to support said third cavity structure.

Further, said super dry fog generator comprises a circuit controller; said circuit controller is connected with said air-blower.

Still further, said super dry fog generator further comprises rollers; a number of said rollers are on the bottom of said shell.

The beneficial effects provided by the technical solutions of the embodiments of the present invention conclude:

In the present invention, the disinfection liquid entering into said atomization device from said liquid-storage device is atomized into small atomized liquid particles by said atomization device, and then the small atomized liquid particles are driven into said dry separation device by said air-blower. After being dried, the small atomized liquid particles are discharged to a space intended to be disinfected, then the disinfection is carried out. The small atomized liquid particles produced by the super dry fog generator of the present invention, whose size is small and much closer to the bacterial size, can be suspended in air for a long time so as to contact fully with the bacteria in air to achieve the purpose of sterilization, and they are convenient and safe with the less corrosion to the objects in the disinfection space. In addition, said super dry fog generator provided in the present invention has a simple structure and a low cost.

BRIEF DESCRIPTION OF THE DRAWINGS

In order to illustrate the technical solutions of the embodiments of the present invention more clearly, a brief description of drawings that assists the description of embodiments of the invention will be provided below. It would be apparent that the drawings in the followings description are only some of the embodiments of the present invention. One skilled in the art will be able to obtain other drawings on the basis of these drawings without paying any creative work.

FIG. 1 is the structure schematic drawing of the super dry fog generator provided in the examples of the present invention, wherein, 1 a liquid-storage device, 11 a through-hole,
2 an air-blower,
3 an atomization device,
4 a dry separation device, 44 an opening,
41 a first cavity structure, 42 a second cavity structure, 43 a third cavity structure,
5 a first bracket,
6 a second bracket,
7 a shell, 71 a perforation, 72 rollers.

DETAILED DESCRIPTION OF THE EMBODIMENT

The embodiment of the present invention will be further described in detail with the aid of the drawings in order to clarify the purpose, the technical solutions and the advantages of the present invention more clearly.

As shown in FIG. 1, the present invention provides a super dry fog generator, and a super dry fog generator comprises a liquid-storage device 1, an atomization device 3, an air-blower 2, and a dry separation device 4 with an opening 44 on the top; wherein the dry separation device 4 is provided over the liquid-storage device 1, and the dry separation device 4 is connected with the liquid-storage device 1; the atomization device 3 is located at the exterior of the liquid-storage device 1; the two ends of the atomization device 3 are connected with the air-blower 2 and the interior of the dry separation device 4, respectively; the atomization device 3 is further connected with the liquid-storage device 1; the liquid entering into the interior of the atomization device 3 is blown into the interior of the dry separation device 4 by the air-blower 2.

Specifically, the dry separation device 4 is connected with the liquid-storage device 1. The liquid to be used for bacteria disinfection is prepared and then is stored in the liquid-storage device 1. The liquid to be used for disinfection enters into the atomization device 3 and is atomized into the small particles by the atomization device 3. The small liquid particles are blown into the dry separation device 4 by the air-blower 2, and then moves up along the inner wall of the dry separation device 4, and finally are discharged into a space intended to be disinfected from the opening 44 on the top of the dry separation device 4. The large liquid particles not being dried condense into a solution along with the inner wall of the dry separation device 4, and then back-flow into the liquid-storage device. The disinfection liquid can be added into the liquid-storage device 1 via the opening 44, i.e. the opening 44 can be used as an inlet for adding the liquid.

In the process of the small liquid particles moving up along the inner wall of the dry separation device 4, they are dried and separated continuously by the blowing driven from the air-blower 2, leading to the further diminishing of the particle size and the further reducing of water content. The size of most liquid particles can reach less than 1 μm, and even part of them can reach 0.1 μm. The small liquid particles can be suspended in air for a long time so as to contact fully with the bacteria in air to achieve the purpose of sterilization. In addition, the corrosion to the equipment in the disinfection space will be greatly reduced by virtue of the reduction of the water content. Moreover, the experimental results show the lower the concentration is, the smaller the size of the atomizing small liquid particles is. Therefore, the usage of the disinfection liquid with low concentration not only greatly reduces the corrosion to the subject in the disinfection space, but also improves the efficiency of the disinfection and sterilization, which is convenient and safe. In addition, the super dry fog generator provided in the present invention has a simple structure and a low cost, which is particularly suitable for the disinfection and sterilization of a closed space, such as GMP cleaning workshops, hospital operation rooms, ICU wards, freeze driers, transferring windows, biosafety cabinets and as the like. Using with the active hydrogen peroxide, there are the merits of no residue and no pollution after sterilization, and it is an ideal disinfection and sterilization equipment replacing formaldehyde.

As shown in FIG. 1, preferably, the dry separation device 4 comprises at least two connected cavity structures, and the bottom of the dry separation device 4 and the top of the liquid-storage device 1 are joined, and the bottom of the dry separation device 4 is connected with the interior of the liquid-storage device 1.

As shown in FIG. 1, preferably, in Examples of the present invention, the dry separation device 4 comprises a first cavity structure 41, a second cavity structure 42 and a third cavity structure 43 which are connected in sequence from bottom to top. The first cavity structure 41, the second cavity structure 42 and said liquid-storage device 1 are in an integrated structure, and the second cavity structure 42 and the third cavity structure 43 are movably joined, and the opening 44 is provided on the top of the third cavity structure 43.

Specifically, the dry separation device 4 comprises at least two connected cavity structures, i.e. at least two stage separators. The shape of the chambers of the cavity structures may be round, square or any other shape. The cavity structures can be joined each other via a tube or a clapboard with holes, and it must ensure that in the process of adding the disinfection liquid into the liquid-storage device 1, the disinfection liquid can completely flow into the liquid-storage device 1 without significant residual; and at the same time it must ensure that the disinfection liquid condensed along with the inner wall of the dry separation device 4 can completely back-flow into the liquid-storage device 1 without significant residual. The openings 44 are provided on the top of the last stage separator (the third cavity structure 43 in the present example), which is to be used as the spray outlet of the dry fog particles of the disinfection liquid (particle size is less than 1 μm) after dried and separated, and at the same time it also is to be used as the inlet of adding the disinfection liquid. The integrated structure of said first cavity structure 41, said second cavity structure 42 and said liquid-storage device 1 can prevent liquid leakage and air leakage.

As shown in FIG. 1, preferably, the atomization device 3 is an atomizing nozzle, and the air-blower 2 is a high-speed hot air motor.

As shown in FIG. 1, preferably, the inlet of the atomizing nozzle is connected with the air outlet of the high-speed hot air motor, and the outlet of the atomizing nozzle is connected with the interior of the first cavity structure 41.

Specifically, in the present example, the high-speed hot air motor blows hot air, which can blow the atomizing small liquid particles into the interior of the dry separation device 4. In the process of the atomizing small liquid particles moving up along the inner wall, they can be easily further dehydrated and the water content can be further reduced, leading to a smaller particle size which is benefit to a sufficient contact with the bacteria in air and a further reducing of the corrosion to the equipment in the disinfection space. A port is provided at the air inlet of the high-speed hot air motor, which is convenient for the connection between the hose and the closed space intended to be disinfected and sterilized, such as freeze dryers, transferring windows, biosafety cabinets, and as the like. Another port is provided at the air outlet of the high-speed hot air motor, which is convenient for the connection with the inlet of the atomizing nozzle via a tube. The atomizing nozzle can be a pneumatic atomizing nozzle. By virtue of the high speed jet air generated by the high-speed hot air motor, the disinfection liquid can be broken and atomized into the small liquid particles for disinfection which then are sprayed into the dry separation device 4.

The atomizing nozzle is preferred to be a two-fluid atomization nozzle (pneumatic nozzle). On the one hand, it is to ensure the formation of negative pressure at the outlet of the disinfection liquid, which is convenient for the inhaling of the disinfection liquid from the liquid-storage device 1 into atomization nozzle; on the other hand, it is to ensure a large atomization area, thereby the small particles of the disinfection liquid sprayed out from the atomization nozzle are diffused and dried sufficiently in the first cavity structure 41 in a large area, to form the smaller disinfection particles. One part of the large particles not being dried enter into the second cavity structure or the third cavity structure 43 to be further dried for forming the smaller particles; the other part of the large particles not being dried are condensed into liquid, and then back-flow into the liquid-storage device 1 for the atomization again. Repeating in such manner as described above, the purpose for complete drying and separation of the large particles and small particles will be achieved.

As shown in FIG. 1, preferably, a through-hole 11 is provided on the bottom of the liquid-storage device 1. The through-hole 11 is connected with the interior of said atomizing nozzle via a tube. The liquid in the liquid-storage device 1 enters the interior of the atomizing nozzle passing through the through-hole 11 and the tube.

Specifically, the liquid-storage device 1 of the present examples is a liquid storage tank which is preferred to be round or square, and there a through-hole 11 in the bottom of the liquid-storage device 1. The liquid-storage device 1 is connected with the atomizing nozzle via a tube. There also can be a liquid level gauge in the liquid-storage device 1 to observe and calculate the atomization volume, and to observe whether there is residual after the atomization of the disinfection liquid being added quantitatively.

As shown in FIG. 1, the super dry fog generator further comprises a shell 7. The liquid-storage device 1, the atomization device 3, the air-blower 2, and dry separation device 4 are all provided in the interior of said shell 7. A perforation 71 is provided on said shell 7, and the air inlet of the high-speed hot air motor is connected with the environment via said perforation 71.

Specifically, each component in this example of the present invention can be fixed due to the setting of the shell 7, and the setting of the perforation 71 can provide air for the high-speed hot air motor.

As shown in FIG. 1, further, said super dry fog generator comprises a first bracket 6 and a second bracket 5. The first bracket 6 is provided between the bottom plate of the interior of the shell 7 and the air-blower 2, so as to support the air-blower 2. The second bracket 5 is provided between the air-blower 2 and the third cavity structure 43, so as to support the third cavity structure 43.

Further, the super dry fog generator comprises a circuit controller. The circuit controller is connected with said air-blower 2.

As shown in FIG. 1, still further, the super dry fog generator comprises rollers 72. A number of the rollers 72 are on the bottom of said shell 7.

In the present example, the practical analysis is carried out by the means of the experiment.

I. Size and Distribution of the Dry Fog Particles

Hydrogen peroxide disinfectant is taken as an example to determine the size of the atomized particles. Because the atomization particles produced in the present invention is very dry and the size of most particles is less than 1 µm, the laser particle spectrum analysers are not suitable for determination in the present invention (note: the technique is only suitable for the determination of particles with size of more than 1 µm). Therefore, the Size and Distribution of the particles were determined by special Airborne Particle Counter.

1. Main Experimental Materials and Apparatus

CLJ-BII(D) Airborne Particle Counter;

6% Hopewei® active hydrogen peroxide disinfectant (sporicide, Executive Standard Q/HHP 001-2015), including 6% hydrogen peroxide and 50 ppm active silver ion (producing by HOPE PHARMA CO., LTD).

2. Test Site

A clean workshop in the GMP plant of pharmaceutical enterprise, wherein the height was 2.8 m, the width was 4.4 m, the length was 6.5 m, and the total volume of the space was about 80 m$^3$.

3. Experiment Method

With the reference of the operating instruction of CLJ-BII (D) Airborne Particle Counter, the experiment was carried out as follows: starting the power switch of Airborne Particle Counter; setting the related parameter (test period: 60 s, sampling unit: 28.3 L/min); setting the sampling ports of the Airborne Particle Counter at 0.25 m, 0.5 m and 1 m away from the atomization outlet of the super dry fog generator to determine the particle size and distribution of the atomization hydrogen peroxide disinfectant.

4. Experiment Result

The determination results of the quantity corresponding to different size of particles are shown in Table 1. The statistical results are shown in Table 2. According to Table 1 and Table 2, the size of most particles, which were produced from the atomization of 6% hydrogen peroxide disinfectant by the present super dry fog generator, is less than 1 µm (more than 60%). The size of the particles mainly distributes in the range from 0.3 µm to 0.5 µm. With the increase of the measured distance, the number of the small particles increases and the number of the large particles reduces; but when the determination distance is more than 0.5 m, the determination results have no significant change. It indicates that after being atomized and dried by the dry fog device of the present invention, the hydrogen peroxide disinfectant became a dry fog in true sense. Theoretically, using the technology provided in the present invention, the particles produced by the primary atomization (less than 10 µm) must become smaller particles (concentrated at least 90%, i.e. less than 1 µm) after being dried and separated, because the concentration of hydrogen peroxide disinfectant is less than 10%. In a disinfectant atomizing and sterilizing device of the prior art, because the atomizing particles contain a large amount of water (more than 90%), the disinfected subject will be moist and then be corroded seriously when the disinfected subject is too closed to the atomization port (less than 1 m) even if the atomized particle size is less than 5 µm.

TABLE 1

The measured result of Size and Cumulative quantity of the particles produced by the atomization of 6% hydrogen peroxide disinfectant in the example of the present invention

| Measured result away from the atomization port 0.25 m | | Measured result away from the atomization port 0.5 m | | Measured result away from the atomization port 1 m | |
|---|---|---|---|---|---|
| ROOM: 02 | | ROOM: 02 | | ROOM: 02 | |
| LOCATION: 02/01 | | LOCATION: 02/01 | | LOCATION: 02/01 | |
| CYCLE: 009/001 | | CYCLE: 008/001 | | CYCLE: 007/001 | |
| DATE: 4 Jan. 2016 | | DATE: 4 Jan. 2016 | | DATE: 4 Jan. 2016 | |
| TIME: 12:35:05 | | TIME: 12:33:45 | | TIME: 12:32:25 | |
| PERIOD: 0060 sec | | PERIOD: 0060 sec | | PERIOD: 0060 sec | |
| VOLUME: 28.30 L | | VOLUME: 28.30 L | | VOLUME: 28.30 L | |
| SIZE | CUMU | SIZE | CUMU | SIZE | CUMU |
| 0.3 µm | 1110884 | 0.3 µm | 1526032 | 0.3 µm | 2040502 |
| 0.5 µm | 1072395 | 0.5 µm | 1448375 | 0.5 µm | 1965789 |
| 1.0 µm | 900641 | 1.0 µm | 1095705 | 1.0 µm | 1526222 |
| 2.0 µm | 780299 | 2.0 µm | 847425 | 2.0 µm | 1182425 |
| 3.0 µm | 697424 | 3.0 µm | 686685 | 3.0 µm | 946487 |
| 5.0 µm | 588102 | 5.0 µm | 499304 | 5.0 µm | 659468 |

TABLE 2

The Distribution Statistics Result of the different size particles

| Size of atomized particle | Measured result at the distance of 0.25 m (percentage) | Measured result at the distance of 0.5 m (percentage) | Measured result at the distance of 1 m (percentage) |
|---|---|---|---|
| 5 µm | 11.4 | 8.2 | 7.9 |
| 3 µm | 13.5 | 11.3 | 11.4 |
| 2 µm | 15.2 | 13.9 | 14.2 |
| 1 µm | 17.5 | 18.0 | 18.3 |
| 0.5 µm | 20.8 | 23.7 | 23.6 |
| 0.3 µm | 21.6 | 25.0 | 24.5 |

II. Disinfection and Sterilization Experiment in the GMP Plant of the Pharmaceutical Enterprise 1. Main Experimental Materials and Apparatus OXYPHARM dry fog sterilization device (produced by OXYPHARM CO., LTD, France, OXY-25000);

biological indicator (the spore of *Bacillus stearothermophilus*, the amount of the spore $10^6$), containing accessional chemistry indicator and TSB liquid culture medium (produced by Beijing Golden Four-ring Technology Co., Ltd.), same as below;

6% Hopewei® active hydrogen peroxide disinfectant (sporicide, Executive Standard Q/HHP 001-2015), same as above;

3% Hopewei® active hydrogen peroxide disinfectant, which is obtained by adding the same volume of water into 6% Hopewei® active hydrogen peroxide disinfectant, same as below.

2. Test Site

A clean workshop in the GMP plant of the pharmaceutical enterprise, wherein the height was 2.8 m, the width was 4.4 m, the length was 6.5 m, and the total volume of the space was about 80 $m^3$.

3. Experiment Method

Using the super dry fog generator provided by the present invention and OXYPHARM dry fog sterilization device respectively, the experiments of the disinfection and sterilization to the 80 $m^3$ workshop in the GMP plant were carried out under the same ambient temperature, the same humidity, the same concentration and amount of hydrogen peroxide disinfectant. According to the size of the workshop, atomization disinfection was carried out in the amount of 5 mL/$m^3$, i.e. using 400 ml Hopewei® active hydrogen peroxide disinfectant. When the atomization was carried out, the two kind devices were located in the middle of the workshop, respectively, 5 pieces of biological indicators were respectively placed in the middle (numbered as 3) and four different corners of the workshop (the two corners in front of the atomizing nozzle were numbered as 1 and 2, respectively; the two corners in back of the atomizing nozzle were numbered as 4 and 5, respectively). All of the biological indicators were located at 1 m away from the ground. After the atomization finished, the workshops were closed for 2 hours. Then the biological indicators (spore strip) were taken out and put into the corresponding numbered liquid culture medium for *Bacillus stearothermophilus*; and then they were put into incubator according to the instructions of the biological indicators and incubated at a temperature range from 50° C. to 55° C. for 48 h. In the meanwhile, a piece of biological indicator in the same batch was taken as the positive control. After being incubated for 48 h, if the culture became turbid and the color of the culture became yellow from purple, it would be determined as 'positive'; if the culture was clear and the color of the culture did not change, it would be determined as 'negative'. Then after being continuously incubated for more 7 days, if there was yet no bacterial growth observed, it would be determined as 'qualified'.

4. Experiment Result

The experiment result was shown in Table 3. According to Table 3, when the amount of spray was 5 mL/$m^3$ and the concentration of the active hydrogen peroxide disinfectant was 6%, the two kind sterilizing devices both could meet the requirements of sterilization, i.e. $10^6$ spores could be killed. However, when the amount of spray was 5 mL/$m^3$ and the concentration of the active hydrogen peroxide disinfectant decreased to 3%, OXYPHARM dry fog sterilization device could not meet the requirements of sterilization, while the super dry fog generator of the present invention could still meet the requirements of sterilization. It indicates that for the disinfection and sterilization of GMP workshops, the super dry fog generator of the present invention has stronger sterilization ability and better sterilization effect, and it is much better than the prior product.

TABLE 3

The comparison of the sterilization effects between the dry fog device of the present invention and the dry fog device purchased from OXYPHARM

| Concentration of hydrogen peroxide | Number of the culture | Test results of the cultures by the super dry fog generator of the present invention | | Test results of the cultures by the dry fog device purchased from OXYPHARM | |
|---|---|---|---|---|---|
| | | 48 h | 7 d | 48 h | 7 d |
| 6% | 1 | purple | purple | purple | purple |
| | 2 | purple | purple | purple | purple |
| | 3 | purple | purple | purple | purple |
| | 4 | purple | purple | purple | purple |
| | 5 | purple | purple | purple | purple |
| | Positive control | yellow | | yellow | |
| 3% | 1 | purple | purple | purple | purple |
| | 2 | purple | purple | purple | purple |
| | 3 | purple | purple | purple | purple |
| | 4 | purple | purple | yellow | yellow |
| | 5 | purple | purple | yellow | yellow |
| | Positive control | yellow | | yellow | |

III. Disinfection and Sterilization Experiment for the Traditional Freeze Dryer

In prior art, the ozone sterilization is usually used in the traditional freeze dryers (without the SIP function) because the traditional freeze dryers cannot endurable in high pressure and is not fit for the steam sterilization. However given the complex internal structure of the traditional freeze dryer, it is difficult to meet the requirements of sterilization by the ozone sterilization. In the present example, a sterilization experiment for the traditional freeze dryer was carried out, using 6% Hopewei® active hydrogen peroxide disinfectant.

1. Main Experimental Materials

The same was as above.

2. The Freeze Dryer for Test

GLZY-13B freeze dryer (produced by Shanghai Pudong CO., LTD) with the function of Cleaning In Place (CIP) and without the function of SIP, wherein the volume of the head box was 3.3 m$^3$, the volume of the rear box was 3.8 m$^3$ and the total volume was about 7.1 m$^3$ (not including the tube).

3. Experiment Method

The freeze dryer was cleaned and dried according to the traditional method, in which 15 pieces of biological indicators (the content of the spores were 10$^6$, respectively) were placed. After closing the door, the air inlet of the head box of the freeze dryer was connected with the atomization outlet ⑫ of the super dry fog generator of the present invention using a hose; the scupper of the rear box of the freeze dryer was connected with the air inlet ⑦ of the super dry fog generator provided by the present invention using a hose. So a closed loop was formed, i.e. the atomized particles of hydrogen peroxide firstly passed through the air inlet of the freeze dryer, and then entered into the head box and the rear box of the freeze dryer in sequence, and then were discharged from the scupper of the rear box of the freeze dryer and entered into the super dry fog generator of the present invention via the air inlet ⑦. The cycle was being repeated. At process of atomization, the freeze dryer was started to make the shelf rise and fall for 1-2 times. After the disinfectant was totally atomized, the device was closed and the freeze dryer was sealed for 2 h, and then the water circulation vacuum pump of the freeze dryer was started, vacuumizing for 30 minutes to remove the residual disinfectant. The biological indicators (spore strip) were respectively taken out and put into the corresponding numbered liquid culture medium for Bacillus stearothermophilus. The methods of incubation and observation were the same as above.

4. Experiment Result

The experiment result was shown in Table 4. According to Table 4, when the concentration of the active hydrogen peroxide disinfectant was 6% and the amount of atomization was 10 mL/m$^3$, the traditional freeze dryer (not having SIP function) could be disinfected and sterilized using the super dry fog generator provided by the present invention, and the requirements of sterilization could be met after sterilization for only 2 h (to cause the spores to reduce 6 log-unit).

TABLE 4

The Detection Results of biological indicators of disinfection and sterilization used in traditional freeze dryer

| Concentration of hydrogen peroxide | Number of the culture | Detection results after 48 h | Detection results after 7 days |
|---|---|---|---|
| 6% | 1 | purple | purple |
|  | 2 | purple | purple |
|  | 3 | purple | purple |
|  | 4 | purple | purple |
|  | 5 | purple | purple |
|  | 6 | purple | purple |
|  | 7 | purple | purple |
|  | 8 | purple | purple |
|  | 9 | purple | purple |
|  | 10 | purple | purple |
|  | 11 | purple | purple |
|  | 13 | purple | purple |
|  | 14 | purple | purple |
|  | 15 | purple | purple |
|  | Positive control | yellow | yellow |

IV. Disinfection and Sterilization Experiment for the Transferring Window

In prior art, because it sometimes need to deliver some certain special subjects (such as pens, record papers and as the like) through the transferring window, the ultraviolet light irradiation is usually used as the disinfection method which cannot meet the requirements of effective sterilization. In the present example, a disinfection and sterilization experiment for the transferring window was carried out, using 3% Hopewei® active hydrogen peroxide disinfectant.

1. Main Experimental Materials and Apparatus

Biological indicators (the spore of Bacillus stearothermophilus, the amount of the spore 10$^6$), containing accessional chemistry indicator and TSB liquid culture medium (Beijing Golden Four-ring Technology Co., Ltd.);

3% Hopewei® active hydrogen peroxide disinfectant, which is obtained by adding the same volume of water into 6% Hopewei® active hydrogen peroxide disinfectant.

2. The Transferring Window for Test

The transferring window was produced by Senlin Co., Ltd, with the Length×Width×Height=0.8 m×1.0 m×0.8 m, and the volume was 0.64 m$^3$.

3. Experiment Method

Firstly, two holes were respectively opened in the top and bottom ends of the one side door of the transferring window, using a hole saw. The size of the holes equaled the size of the inlet and the outlet of the super dry fog generator provided in the present invention. Then the hole in the bottom of the transferring window was connected with the air outlet ⑫ of the super dry fog generator using a hose, and the hole in the top of the transferring window was connected with the air inlet ⑦ of the super dry fog generator using a hose. Therefore a closed circuit was formed, i.e. the atomized particles of hydrogen peroxide firstly entered into the transferring window via the hole in the bottom of the transferring window, and then entered into the super dry fog generator via the hole in the bottom of the transferring window and the air inlet ⑦ of the super dry fog generator in sequence. The cycle was being repeated. After 4 mL of 3% Hopewei® active hydrogen peroxide disinfectant was added and atomized, the device was closed and sealed for 2 h. And then the biological indicators (spore strip) were taken out and put into the corresponding numbered liquid culture medium for Bacillus stearothermophilus; and then they were incubated at a temperature range from 55° C. to 60° C. In the meanwhile, a piece of biological indicator in the same batch was taken as the positive control. After being incubated for 48 h, if the culture became turbid and the color of the culture became yellow from purple, it would be determined as 'positive'; if the culture was clear and the color of the culture did not change, it would be determined as 'negative'. After being continuously incubated, if the color of the culture remained purple, it would be considered as 'no bacterial growth'.

4. Experiment Result

The experiment result was shown in Table 5. According to Table 5, when the concentration of the active hydrogen peroxide disinfectant was 3% and the amount of atomization was 5 mL/m$^3$, the transferring window could be sterilized using the super dry fog generator provided by the present invention, and the requirements of sterilization could be met (to cause the spores to reduce 6 log-unit).

TABLE 5

The detection results of biological indicators for the sterilization and sterilization of the transferring window

| Concentration of hydrogen peroxide | Location of biological indicator | Detection results after 48 h | Detection results after 7 days |
|---|---|---|---|
| 3% | The top of the transferring window | purple | purple |
| | The middle of the transferring window | purple | purple |
| | The bottom of the transferring window | purple | purple |
| | Positive control | yellow | yellow |

Over all, the present invention has the following advantages:

1. Due to the usage of an atomization system containing the high-speed hot air motor and two-fluid atomization nozzle, not only the cost is lower, but also the atomized particles of the disinfectant can be concentrated and dried by the hot air from the high-speed hot air motor.

2. The dry separation device 4 (including a primary separator, a second separator, and a third separator) is used for the first time, by which the atomized particles of the disinfectant from the atomizing nozzle (less than 10 μm) are dried and separated for several times, making the large particles being dried to form the small particles or being aggregated to a liquid back-flowing into the liquid-storage device 1 for being atomized again to form small particles.

3. When hydrogen peroxide disinfectants are adopted and the concentration of the hydrogen peroxide disinfectant is less than 10%, the particles of the disinfectant finally produced in the present invention are less than 1 μm; when hydrogen peroxide disinfectants are adopted and the concentration of the hydrogen peroxide disinfectant is 6%, the particles of the disinfectant finally produced in the present invention are less than 0.5 μm (mainly at a range from 0.3 μm to 0.5 μm). Theoretically, when hydrogen peroxide disinfectants are adopted and the concentration of the hydrogen peroxide disinfectant is less than 1%, the particles of the disinfectant finally produced in the present invention are less than 0.1 μm (reaching a nano-size). Thus the technology of the present invention is better than all the prior atomization technology of the hydrogen peroxide disinfection liquid, and also is better than the atomizing inhalation technology widely used in clinical practice, such as the atomizing inhalation technology used for prevent and treat interstitial plasma cell pneumonia whose the atomization particles size range only from 1 μm to 5 μm.

4. When the technology of the present invention is used for the disinfection and sterilization of the space and hydrogen peroxide disinfectants are adopted, the working concentration of hydrogen peroxide disinfectant can be decreased to below 3%. Therefore the corrosion of hydrogen peroxide to epoxy floors and color plates is greatly reduced and the efficiency of disinfection and sterilization is improved.

5. The technology of the present invention can be used for the disinfection and sterilization of not only rooms, such as GMP cleaning workshops, hospital operation rooms, and ICU sickrooms, but also the closed chamber, such as freeze dryers, transferring windows, biosafety cabinets and as the like.

6. When the technology of the present invention is used for the disinfection and sterilization of GMP cleaning workshops, there will not be corrosion even if the distance between the opening 44 of the top of the dry separation device 4 and the color steel plate wall or the epoxy floor is less than 0.5 m. The reason is that the particle sizes of hydrogen peroxides produced by the technology of the present invention are less than 1 μm, and the particles are water-free and completely dry fog particles. The particle size can be determined by Airborne Particle Counter. However, when hydrogen peroxide disinfectants are used cooperatively with the prior dry fog technology for the disinfection and sterilization of the workshop, such as the hydrogen peroxide dry fog device produced by French OXYPHARM company (model: OXY-2500, the size of the particles produced is about 5 μm), the distance between the atomizing outlet and the color steel plate wall or the epoxy floor must be more than 2 m in order to avoid corrosion, because the atomized particles contain a large amount of water; in particular, when the distance between the atomizing outlet and the color steel plate walls is less than 1 m, the color steel plate walls will be soaked and a strong corrosion will be observed, and the atomized particle size cannot be determined by Airborne Particle Counter because the detector will be soaked causing serious pollution.

7. Being used for the disinfection and sterilization, the technology of the present invention is safe and efficient, with a continuous sterilization process, a short cycle period, harmlessness to the human body and no damage to the surface of devices, walls and floors. When hydrogen peroxide disinfectants are used cooperatively with the device provided in the present invention, there are no residue and no pollution after atomization. Thus the device of the present invention is a green environmental protection disinfection equipment, which can completely replace formaldehyde disinfection.

The above is only preferred examples of the present invention, and is not limited to the scope of the present invention. Any modification, equivalent substitution, improvement and as the like, are all included in the protection scope of the present invention.

The invention claimed is:

1. A super dry fog generator comprising a liquid-storage device, an atomization device, an air-blower and a dry separation device; wherein the dry separation device comprises a top and a bottom, and an opening on the top; wherein the dry separation device is above the liquid-storage device and connected with the liquid-storage device; wherein the atomization device is located at an exterior of the liquid-storage device and comprises two ends; wherein the two ends of the atomization device are connected with the air-blower and an interior of the dry separation device, respectively; wherein the atomization device is connected with the liquid-storage device, and a liquid entering into an interior of the atomization device is blown into the interior of the dry separation device by the air-blower, wherein the dry separation device comprises at least two connected cavity structures; and wherein the bottom of the dry separation device is joined to a top of the liquid-storage device and connected with an interior of the liquid-storage device.

2. The super dry fog generator according to claim 1, wherein the dry separation device further comprises a first cavity structure, a second cavity structure and a third cavity structure connected in sequence from bottom to top; wherein the first cavity structure, the second cavity structure and the liquid-storage device are in an integrated structure, and the second cavity structure and the third cavity structure are movably joined; and wherein an opening is on a top of the third cavity structure.

3. The super dry fog generator according to claim 2, wherein the atomization device is an atomizing nozzle, and the air-blower is a high-speed hot air motor.

4. The super dry fog generator according to claim 3, wherein an inlet of the atomizing nozzle is connected with an air outlet of the high-speed hot air motor, and an outlet of the atomizing nozzle is connected with an interior of the first cavity structure.

5. The super dry fog generator according to claim 4, wherein there is a through-hole at a bottom of the liquid-storage device connected with an interior of the atomizing nozzle via a tube; and wherein the liquid from the interior of the liquid-storage device enters into the interior of the atomizing nozzle after passing through the through-hole and the tube.

6. The super dry fog generator according to claim 5, wherein the super dry fog generator further comprises a shell having a perforation thereon; and wherein the liquid-storage device, the atomization device, the air-blower and the dry separation device are each in an interior of the shell, and an air inlet of the high-speed hot air motor is connected with an environment through the perforation.

7. The super dry fog generator according to claim 6, wherein the super dry fog generator further comprises a first bracket and a second bracket; and wherein the first bracket is between a bottom plate of the interior of the shell and the air-blower so as to support the air-blower, and the second bracket is between the air-blower and the third cavity structure so as to support the third cavity structure.

8. The super dry fog generator according to claim 7, wherein the super dry fog generator further comprises a circuit controller connected with the air-blower.

9. The super dry fog generator according to claim 8, wherein the super dry fog generator further comprises rollers, and a number of the rollers are on a bottom of the shell.

* * * * *